(12) United States Patent
Bacon

(10) Patent No.: US 7,553,332 B2
(45) Date of Patent: Jun. 30, 2009

(54) EXPANDABLE, SUPPORTING ACETABULAR CUP

(76) Inventor: Roger Bacon, 912 Main road, Hudson, Québec (CA) J0P 1H0

( * ) Notice: Subject to any disclaimer, the term of this patent is extended or adjusted under 35 U.S.C. 154(b) by 720 days.

(21) Appl. No.: 11/060,402

(22) Filed: Feb. 18, 2005

(65) Prior Publication Data

US 2005/0171614 A1   Aug. 4, 2005

Related U.S. Application Data

(63) Continuation of application No. PCT/CA03/01270, filed on Aug. 20, 2003.

(30) Foreign Application Priority Data

Aug. 22, 2002   (CA) .................................... 2400955

(51) Int. Cl.
*A61F 2/32*   (2006.01)
(52) U.S. Cl. .................... 623/22.3; 623/22.26
(58) Field of Classification Search ... 623/22.11–22.38, 623/19.11–19.14, 22.1, 23.39
See application file for complete search history.

(56) References Cited

U.S. PATENT DOCUMENTS

| | | | | |
|---|---|---|---|---|
| 3,818,512 | A * | 6/1974 | Shersher ................... | 623/22.15 |
| 3,977,026 | A * | 8/1976 | Battault .................... | 623/22.26 |
| 4,519,101 | A * | 5/1985 | Schreiber et al. ........... | 623/22.3 |
| 4,662,891 | A * | 5/1987 | Noiles ..................... | 623/22.31 |
| 4,828,565 | A * | 5/1989 | Duthoit et al. ............. | 623/22.3 |
| 4,834,759 | A * | 5/1989 | Spotorno et al. ........... | 623/22.3 |
| 4,961,748 | A * | 10/1990 | Frey et al. ................ | 623/22.21 |
| 5,108,446 | A * | 4/1992 | Wagner et al. ............. | 623/22.28 |

(Continued)

FOREIGN PATENT DOCUMENTS

EP   0 900 552   3/1999

(Continued)

*Primary Examiner*—Corrine McDermott
*Assistant Examiner*—Cheryl Miller
(74) *Attorney, Agent, or Firm*—Ogilvy Renault LLP

(57) ABSTRACT

The invention relates to an expandable acetabular cup (46) which is designed to eliminate the difficulties associated with positioning in the acetabulum of the patient. The inventive device comprises a hemispherical acetabular cup (46) which is partially slotted at six points to facilitate the expansion of a core with conical fitting. The expandable acetabular cup (46) is designed such that it can be introduced freely, or with slight pressure, into a preformed bone cavity. The conical core (16) is designed to be fixed to a guide/impacteur graduated in degrees to maximize the desired position. The implantation is performed gradually. The inclination and anteversion can be checked at all times during the implantation. The retaining mechanism of the guide/impacteur can be used to remove the conical core (16) to re-position the acetabular cup (46) if necessary. The expandable acetabular cup (46) can receive a conical auto-blocking core (85A, 85C) or, according to the patient' condition, a conical core (16) and a supporting auto-blocking ring (26), preferably pre-assembled to facilitate the chirgien's task. The device is secured in final position thereof using the thongs (86A, 96C) of the conical core (85A, 85C), which are disposed in the ribs (20) of a compressed expandable acetabular cup (46) in the acetabulum of the patient. It is recommended to use a femoral head (36) whose diameter is a function of the exterior diameter of the expandable acetabular cup, to therefore obtain the optimal thickness of the conical core (16) and to conserve the required thickness of the acetabular cup (46).

15 Claims, 10 Drawing Sheets

U.S. PATENT DOCUMENTS 5,108,448 A * 4/1992 Gautier .................... 623/22.26
5,571,201 A * 11/1996 Averill et al. ............ 623/22.22
5,725,589 A * 3/1998 Pfaff et al. ............... 623/22.29
5,976,148 A * 11/1999 Charpenet et al. ............. 606/91
6,620,200 B1 * 9/2003 Descamps et al. ........ 623/22.32
6,811,569 B1 * 11/2004 Afriat et al. .............. 623/22.32
2004/0093090 A1 * 5/2004 Barbieri et al. ............ 623/22.3

FOREIGN PATENT DOCUMENTS

FR     WO 01/35873    *   5/2001

* cited by examiner

EXPANDABLE, SUPPORTING ACETABULAR CUP

RELATED APPLICATION(S)

This application is a Continuation of PCT Parent Application No. PCT/CA2003/01270 filed Aug. 20, 2003 claiming priority on Canadian Patent Application No. 2,400,955 filed Aug. 22, 2002.

BACKGROUND OF THE INVENTION

1. Field of the Invention

The present invention generally pertains to positioning and maintaining an expandable acetabular cup in a bone cavity. The present invention finds a particularly advantageous application in inserting an acetabular cup in the field of cementless hip prosthetics.

2. Description of the Prior Art

Presently known as acetabular implants comprising a hemispherical acetabular cup of the type that are "press fit". This type of acetabular cup is implanted in a bone cavity previously enlarged by simple impaction or compression. By positioning the acetabular cup in the bone cavity under pressure it is unfortunately not possible to proceed with a gradual entry of the acetabular cup in the cavity which would permit to correct positioning errors. Therefore, a plurality of press fit acetabular cups are inadequately implanted such that it is not possible to rectify the situation while preserving the integrity of the bone tissue bordering the prosthetic implant.

The difficulties of positioning the acetabular cup in the acetabulum of the patient are principally caused by the installation of the acetabular cup in the bone with a high level of constraints for obtaining optimal implant stability.

Moreover, the configuration of the hemispherical part of the acetabular cup can damage the bone surface during a forced implantation by way of a guide/impacteur. What's more, screws often need to be installed in the bone to assure the primary stability of the implant.

SUMMARY OF THE INVENTION

In this perspective, one of the objectives of the present invention is to provide an acetabular cup that is insertable and retractable in a bone cavity destined to receive the implant.

Another objective of the present invention is to provide an acetabular cup having radial flexibility permitting free insertion into a bone cavity.

A further objective of the present invention is to allow for the repositioning of an acetabular cup inserted out of position.

Still another objective of the present invention is to provide an acetabular cup being freely insertable into a bone cavity without damaging the tissue bordering the latter.

These objectives, as well as other objectives that will be made apparent further on, are fulfilled by an acetabular implant comprising an acetabular cup defining an internal cavity for receiving a conical core, said acetabular cup being expandable and radially retractable respectively by the insertion and retraction of said core.

According to a preferred embodiment of the present invention, the acetabular cup is cut into sectors by slots oriented along meridian planes.

Following one characteristic of the present invention, the new concept of positioning consists of inserting an expandable acetabular cup with the same diameter or with a slight constraint with respect to the enlargement of the acetabulum. The conical core is gradually driven into the acetabular cup up until an acceptably rigid position is obtained to permit the verification of the inclination and of the antiversion. At this stage the acetabular cup can be repositioned to its nominal position with a variation of less than 5°.

Maximally driving a conical core into the acetabular cup permits the expandable walls of the acetabular cup to expand radially. Each stop of the conical core being insertable in the cavities of the expandable acetabular cup for a secure fit. The replacement of an expandable and retractable acetabular cup is facilitated by retracting the conical core, which has the effect of liberating the constraints of the bone cavity.

The installation of a retentive acetabular cup, that simulates the human condition, is limited by the reduction of ROM (range of motion) when a femoral head is utilized, whereby the neck is half the femoral head.

Based on Bergmann's study[1], that permitted the evaluation of contact forces at the hip in vivo during daily activities, it has been established that the reduction of the neck of the femoral stem, according to the weight of the patient and to the diameter of the acetabular cup, can augment the ROM significantly so that the patient may practice their daily activities. It is known that a hip needs 113 degrees of flexion to function normally.

[1] G. Bergman et al., 2001, <<hip contact forces and gait pattern from routine activities>>Journal or Biomechanics, 34, P. 859-871

The patient's weight increases with the diameter of the acetabular cup; and the diameter of the neck of the femoral stem must be increased in proportion with the weight applied on the femoral stem. The diameter of the femoral head may also be changed proportionally to the acetabular cup diameter, which will increase the ROM.

According to the following table, the exterior diameter of the expanded acetabular cup may be determined by considering a 6 mm thick core and a 5 mm thick acetabular cup wall.

| Femoral Head diameter (mm) | Acetabular cup diameter (mm) | ROM | Femoral stem diameter (mm) | Patient's weight (Kg) |
| --- | --- | --- | --- | --- |
| 28 | 50-52 | 127° | 10.5 | 65 or > |
| 32 | 54-56 | 130° | 11.5 | 75 |
| 36 | 58-60 | 131° | 12.5 | 85 |
| 40 | 62-64 | 132° | 14 | 95 or < |

For a retentive acetabular cup, a 4 mm thick core, a 3 mm cobalt-chrome ring and a 5 mm thick expandable acetabular cup wall can be used to obtain a total diameter thickness of 24 mm. The 24 mm combined thickness is added to the femoral head diameter and this measurement is used to obtain the appropriate expandable acetabular cup diameter. The constraining action of the retaining ring may vary by 0.4 mm, depending on the size of the femoral head.

| Femoral head diameter (mm) | Acetabular cup diameter (mm) | ROM | Femoral stem diameter (mm) | Patient's weight (Kg) |
| --- | --- | --- | --- | --- |
| 28 | 52-54 | 118° | 10.5 | 65 or > |
| 32 | 56-58 | 121° | 11.5 | 75 |
| 36 | 60-62 | 122° | 12.5 | 85 |
| 40 | 64-66 | 123° | 14 | 95 or < |

BRIEF DESCRIPTION OF THE DRAWINGS

Reference will now be made to the accompanying drawings, showing by way of illustration a preferred embodiment thereof, and in which.

DESCRIPTION OF THE PREFERRED EMBODIMENTS

Figure 1:
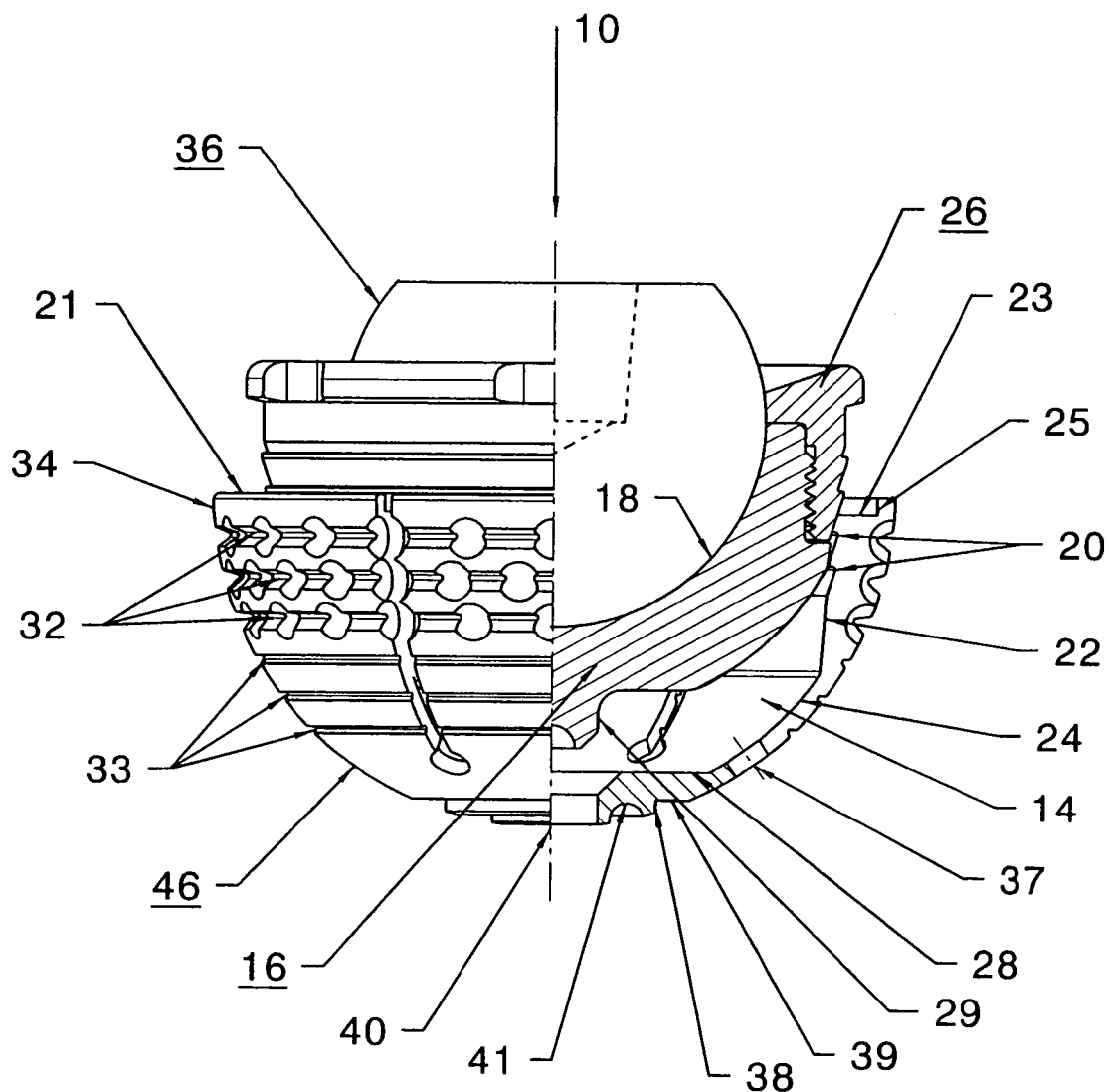
FIG. 1 is a partially sectioned view representing the subassembly of the core, of the femoral head and of the threaded constrained ring in a pre-assembled position in the expandable and retractable acetabular cup, comprising two ribs, in accordance with a first embodiment of the present invention.
Figure 2:
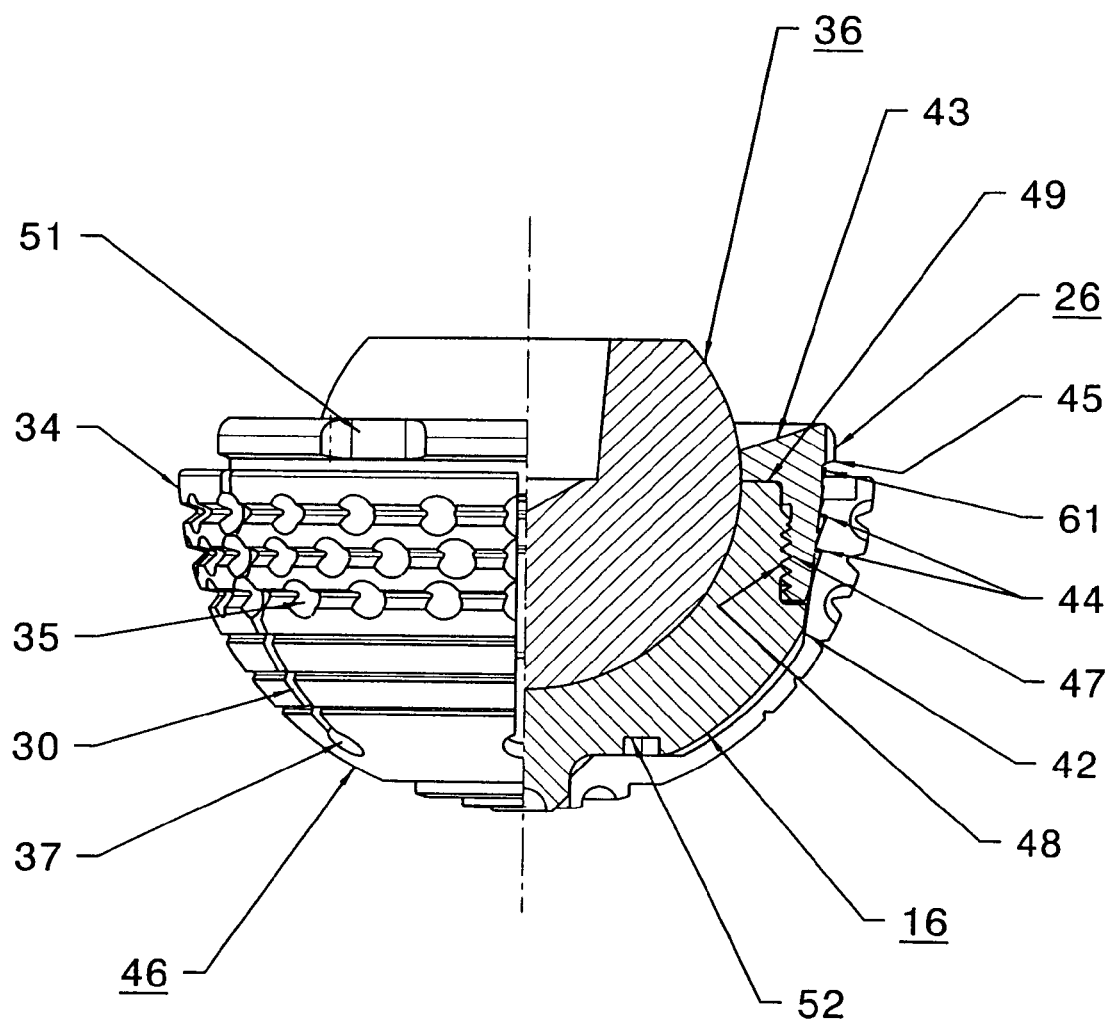
FIG. 2 is a partially sectioned assembly view, illustrating the acetabular cup in expansion under the effect of the core and of the threaded retaining ring, with the femoral head in position in the core.

FIGS. 1 and 2 illustrate an acetabular implant 10 comprising an expandable and retractable acetabular cup 46 defining an internal cavity 14 in which is engaged a core 16. The core 16 having a housing 18 destined to receive a femoral head 36. The femoral head 36 is retained in the housing 18 by at least a threaded retaining ring 26.

The acetabular cup has a generally hemispherical exterior profile for fixation in the acetabulum previously prepared with hemispherical cutting heads of a known diameter. According to a characteristic of the present invention, the acetabular cup 46 is dimensioned for a free entry or with a slight pressure into the acetabulum. The anchorage of the acetabular cup 46 in the bone cavity is subsequently assured by the radial expansion of the acetabular cup 46 resulting in the insertion of the core 16 in the internal cavity 14 of the acetabular cup 46.

Figure 3:
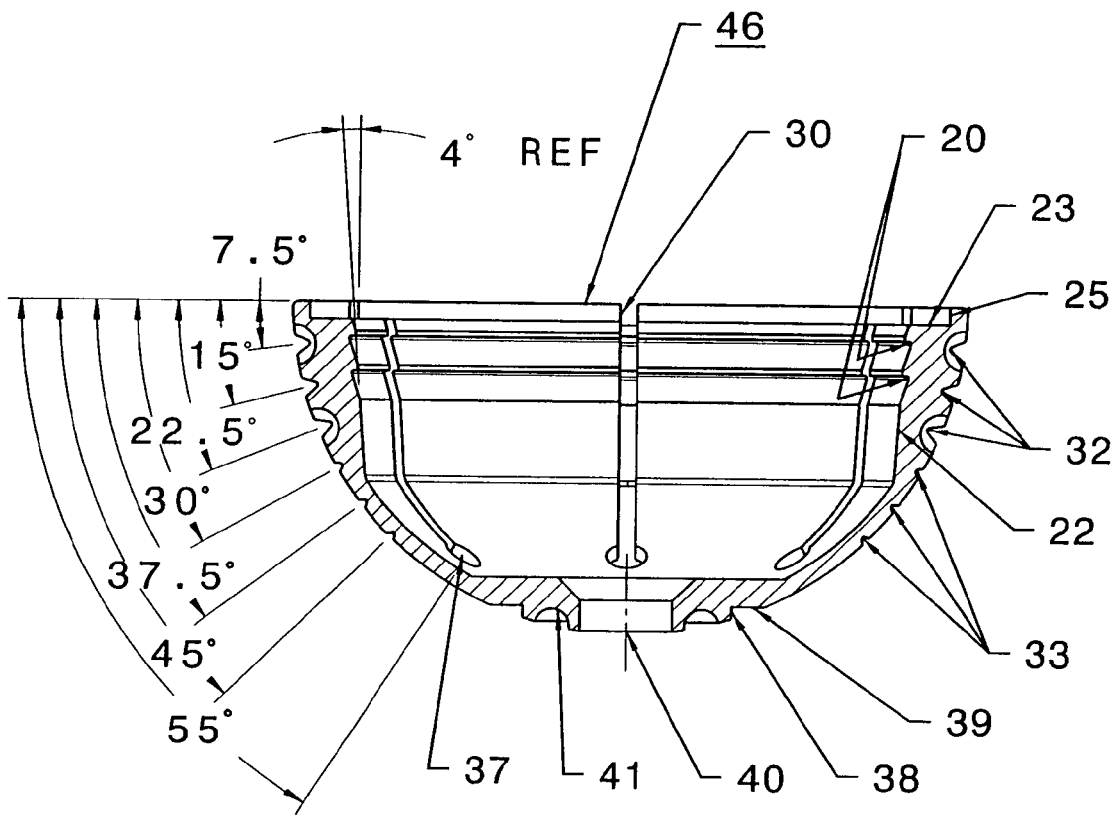
FIG. 3 is a sectioned view of the expandable acetabular cup.

The expandable acetabular cup 46 is provided in biocompatible materials such as titanium or high density polyethylene. These biocompatible materials help produce the flexible section. The acetabular cup 46 features a peripheral rim 21 delimiting the entry of the internal cavity 14. The rim 21 possesses a frusta conical cone internal surface 22 (see FIGS. 1 and 3) having, for example, a taper of approximately 4°. As depicted in FIGS. 1, 2 and 3 the rim 31 has an increasing thickness. The internal surface 22 of rim 21 defines two angular ribs 20 and extends in a smooth internal surface 24, forming the profile of a sphere to terminate in the flat bottom 28 defining a central hole 40.

The acetabular cup 46 is cut into sectors by way of slots 30 oriented along meridian planes. According the exemplary embodiment, six slots 30 are uniformly spaced along the circumference of the acetabular cup 46 and penetrate at an angle of 55° towards the bottom from the opening of the plane 21 of the acetabulum. Still in accordance with the preferred embodiment, the slots 30 define in between themselves an angle of 60°. The purpose of the slots 30 is to facilitate the radial expansion of the acetabular cup 46 by the core 16 and the retentive ring 26. Circumferential ribs 32 are defined on the external surface of the flexible part of the acetabular cup 46 and hemispherical cavities 35 are disposed on the interior of the ribs 32 to facilitate the anchorage of the bone cavity after the acetabular cup 46 has been radially dilated. The ribs 32 are, in part, parallel to each other, and also parallel to the equatorial opening plane of the acetabular cup 46. The ribs 32 are disposed in the hemispherical part at depths that may vary depending on the thickness of the walls of the acetabular cup 46. For example, the ribs 32 may be distributed at a depth of approximately 22.5° from the opening plane of the acetabular cup 46. According to the embodiment illustrated in FIG. 3, a first rib 32 may be localized at 7.5°, a second at 15° and a third at 22.5°. Additional ribs 33 may also be defined at 30°, at 37.5° and at 45° (FIG. 3). A circumferential rib 41 is defined in the exterior surface of the flat bottom 28 about the central hold 40 so as to improve the anchorage of the acetabular cup 46 in the acetabulum. Each slot 30 terminates in an enlarged hole 37. The holes 37 and the ribs 33 contribute to increasing the flexibility of each segment of the acetabular cup 46. An annular shoulder 39 having an internal rim 38 exists to facilitate manipulation of the acetabular cup 46 during its fabrication. An annular surface 23, bordered by an exterior lip 25, is formed in the top surface of the superior rim 21 of the acetabular cup 46 so as to serve as a support for a tool that will be used to remove the ring 26 and the conical core 16 if necessary.

The core 16 may be composed of a high density polyethylene and features a frustralconical portion 42 having a superior taper to the taper of the internal surface 22 of the acetabular cup 46. For example, for a 6° taper of the frustra conical portion 42, a taper of 4° to 5° of the internal surface 22 of the acetabulum permits to spread the pressure in priority on the peripheral rim. As illustrated in FIG. 2, the ring 26 possesses a frusta conical portion 61, in cascade, permitting the radial expansion of the acetabular cup 46, up to 1 mm, by maximally driving the core 16 and the ring 26, up to the surface 28 in the bottom of the acetabular cup 46. The frusta conical portion 61 defines two stops 44 created to house the angular ribs 20 of the acetabular cup 46 in expansion to secure the femoral head 36 in place.

The core 16, the femoral head 36 and the threaded ring 26 should preferably be preassembled to decrease the operating time. The threads 47 of the ring 26 are adjustable with respect to the threads 48 of the core 16 and allow the ring 26 to be supported by the surface 49 of the core 16 to control the axial game of the femoral head 36. External ribs 51 of the same as in the cavities 52 respectively exist at the top of the threaded ring 26 and at the base of the core 16 so as to serve as maintenance points during pre-assembly. Ribs 51 are created so that the orienting impactor can come into contact with the flaring surface 43 of the ring 26 during the implantation of the sub-assembly of the core 16 in the acetabular cup 46. The ring 26 has a rim 45 on which a tool can be supported thereby to remove the core assembly of the acetabular cup 46 when needed. A pivot 29 extends on the inferior surface of the core 16 engageable by sliding into the central hole 40 so as to guide the core 16 during the insertion into the acetabular cup 46.

Figure 4:
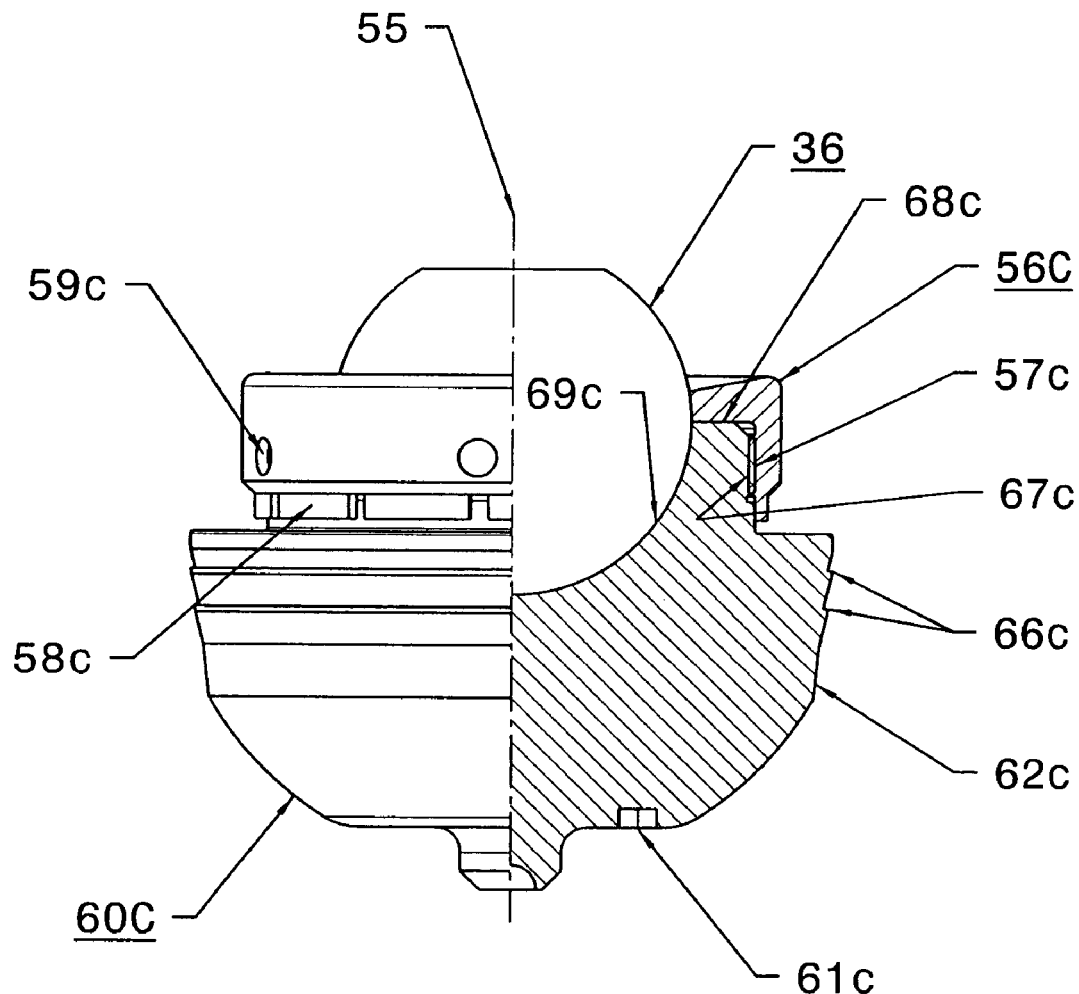
FIG. 4 is a partially sectioned view representing an alternative sub-assembly of a supporting core according to a second embodiment of the present invention.

The sub-assembly 55 of the retentive core 60c, as represented in FIG. 4, is an alternative model in which the neck possesses external threads 67c engageable with internal threads 57 of the ring 56c. The ring 56c is screwed onto the neck of the core 60c until the ring 56c comes into contact with the surface 68c of the core 60c. Tongs 58c are distributed along the circumference of the inferior extremity of the ring 56c. The blades 58c come into contact, applying a slight pressure, on the neck of the core 60c to secure the femoral head 36 in position. The cavities 59c in the retentive ring 56c in the bottom of the core, serve as a preassembly of the threaded retentive acetabular cup. The retaining ring 56c is preferably installed in the factory to obtain an appropriate adjustment and therefore decrease the operating time. The conical surface 62c of the core 60c serves to expand the surface 22 of the expandable acetabular cup 46 illustrated in FIG. 3. The two circumferential stops 66c of the core 60c engage with the angular ribs 20 of the acetabular cup 46 when expanded.

Figure 5:
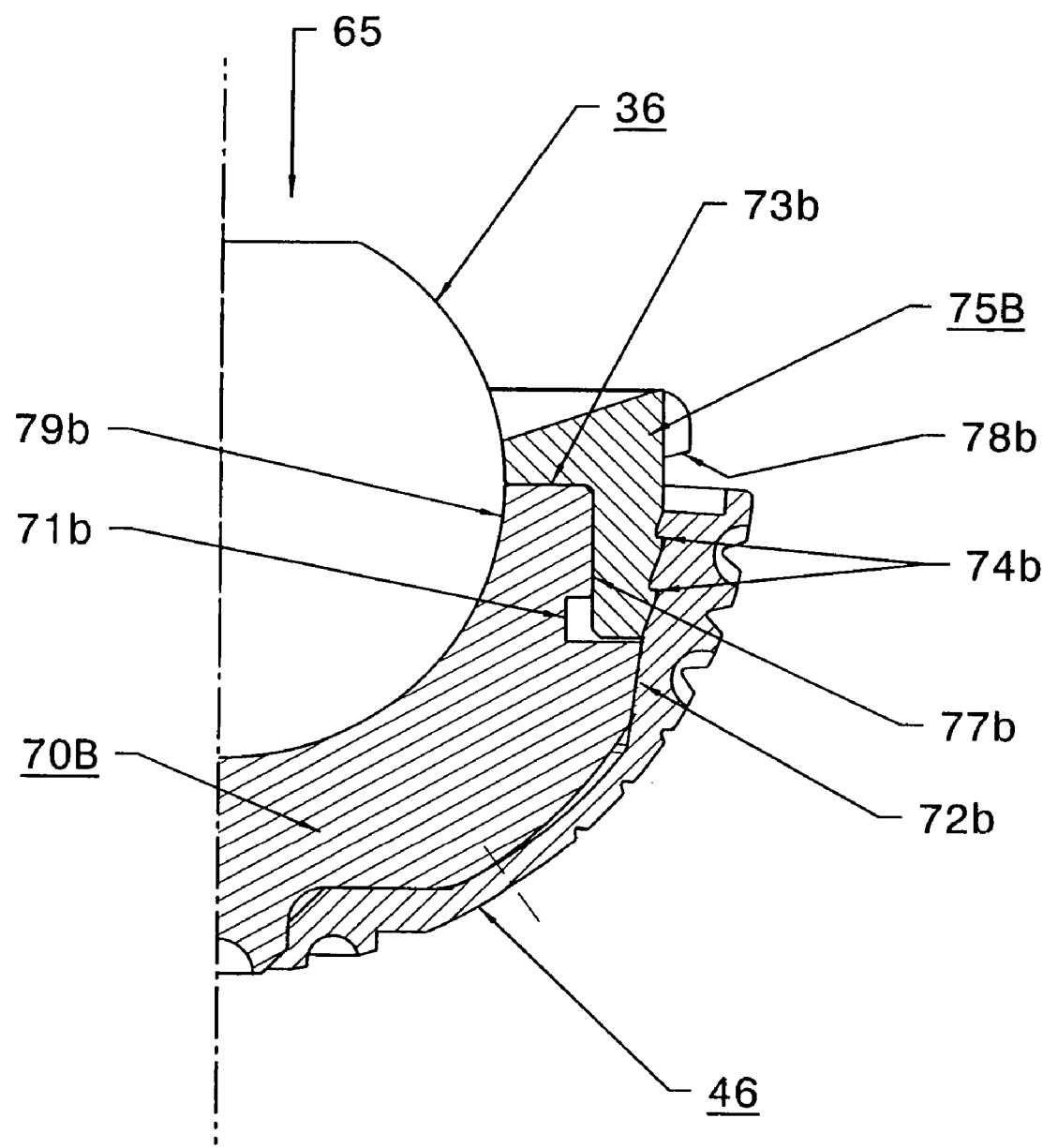
FIG. 5 is a sectioned view that represents a facultative assembly of a supportive acetabular cup according to a third embodiment of the present invention.
Figure 10:
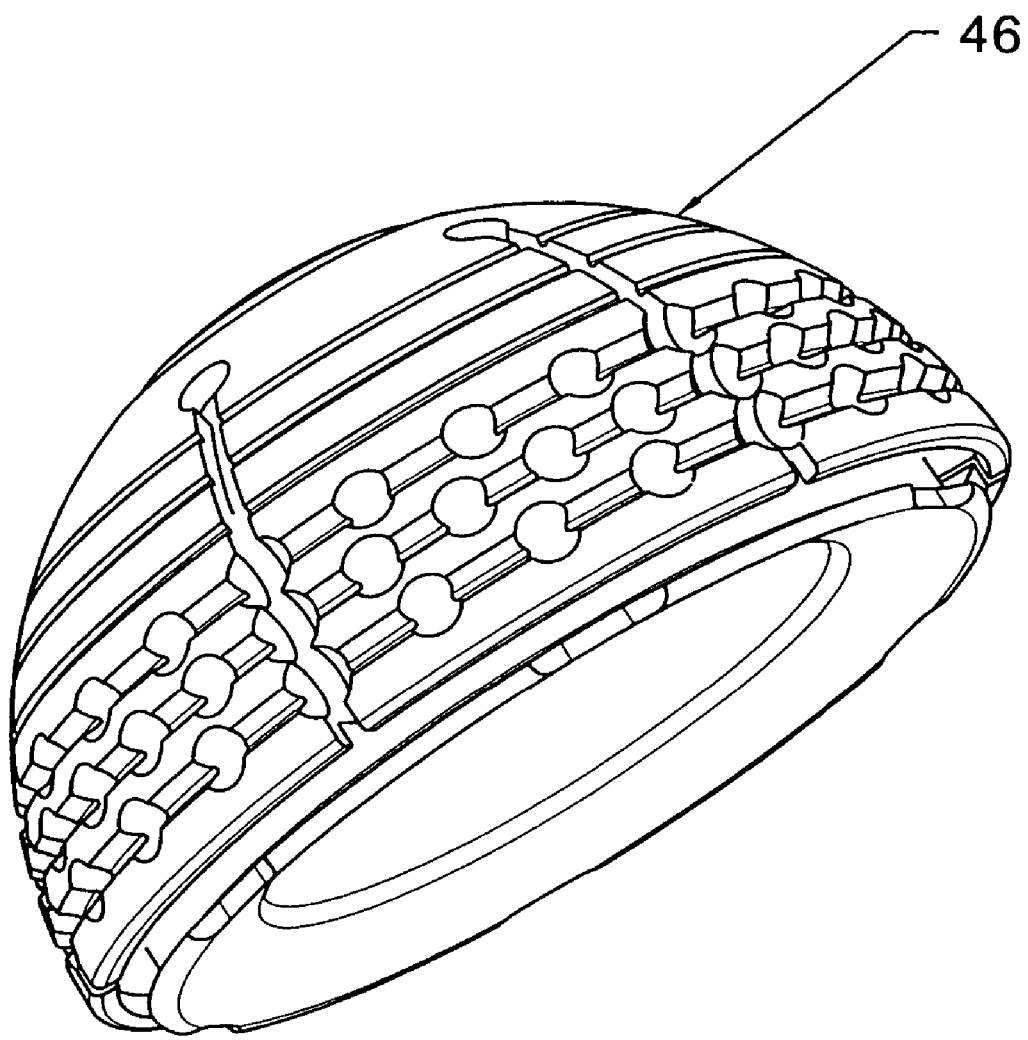
FIG. 10 represents an acetabular cup installed according to a recommended position.

The alternative assembly 65 of the core, as illustrated in FIG. 5, permits the installation of each component by the surgeon. The acetabular cup 46 may be freely inserted or inserted with a slight pressure in the bone cavity with the help of a guide graduated in degrees according to the desired orientation, as illustrated in FIG. 10. The conical core 70b is inserted with a slight pressure with the help of a graduated guide/impacteur that is retained and oriented by the rib 71b, in the slightly expanded acetabular cup 46 until obtaining the desired position. Next, the femoral head 36 is inserted in the housing 79b of the core 70b. The ring 75b is finally inserted in position with the precise adjustment of the diameter 77b until it comes into contact with the surface 73b. The stops 74b of the ring 75b engage with the angular ribs 20 of the expanded acetabular cup 46 to secure the femoral head 36 in position.

Figure 6:
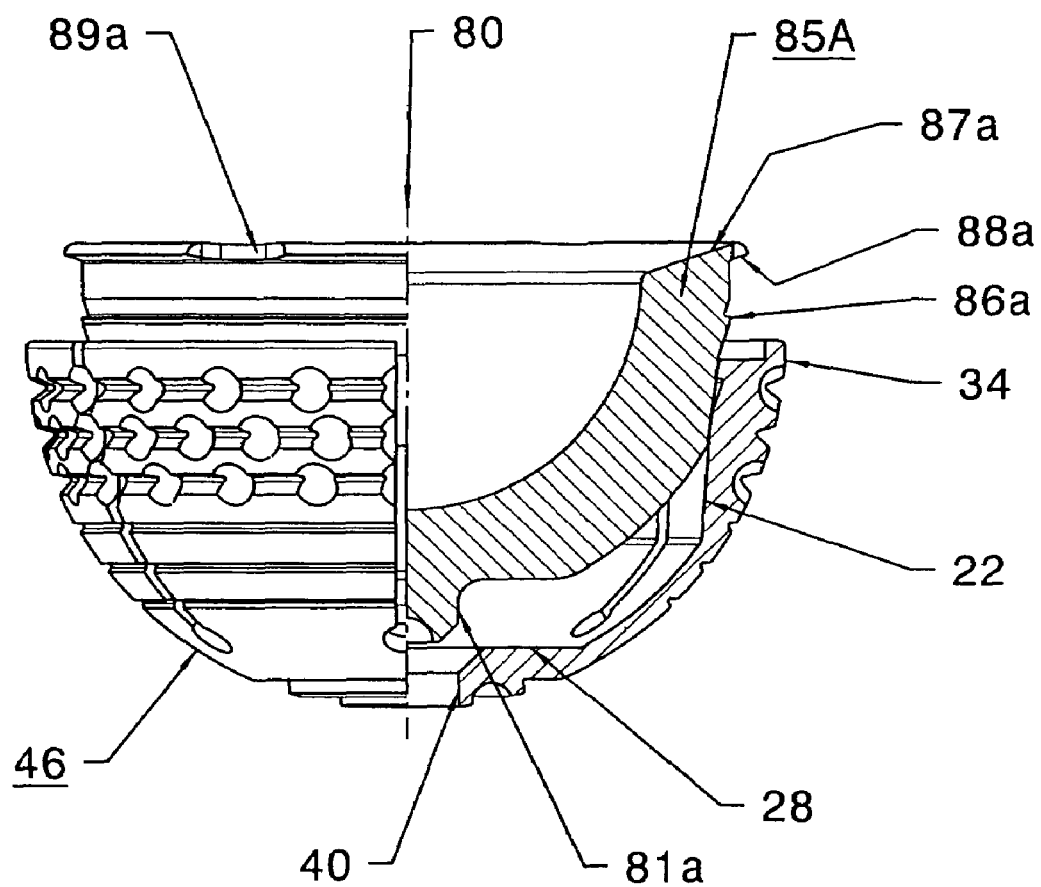
FIG. 6 is a partially sectioned view representing the pre-assembly of a autoblocking core, comprising a stop, in a non-expanded acetabular cup, according to a fourth embodiment of the present invention.
Figure 7:
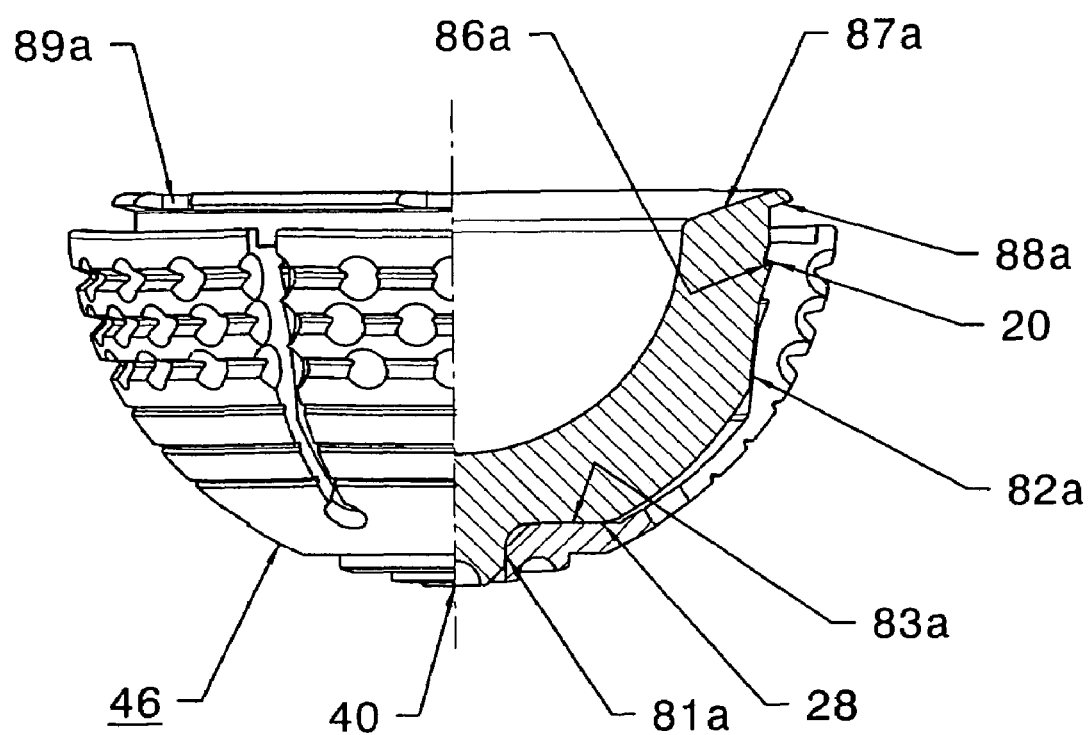
FIG. 7 is a partially sectioned view representing the assembly of the core in FIG. 6 positioned in the expandable acetabular cup.
Figure 8:
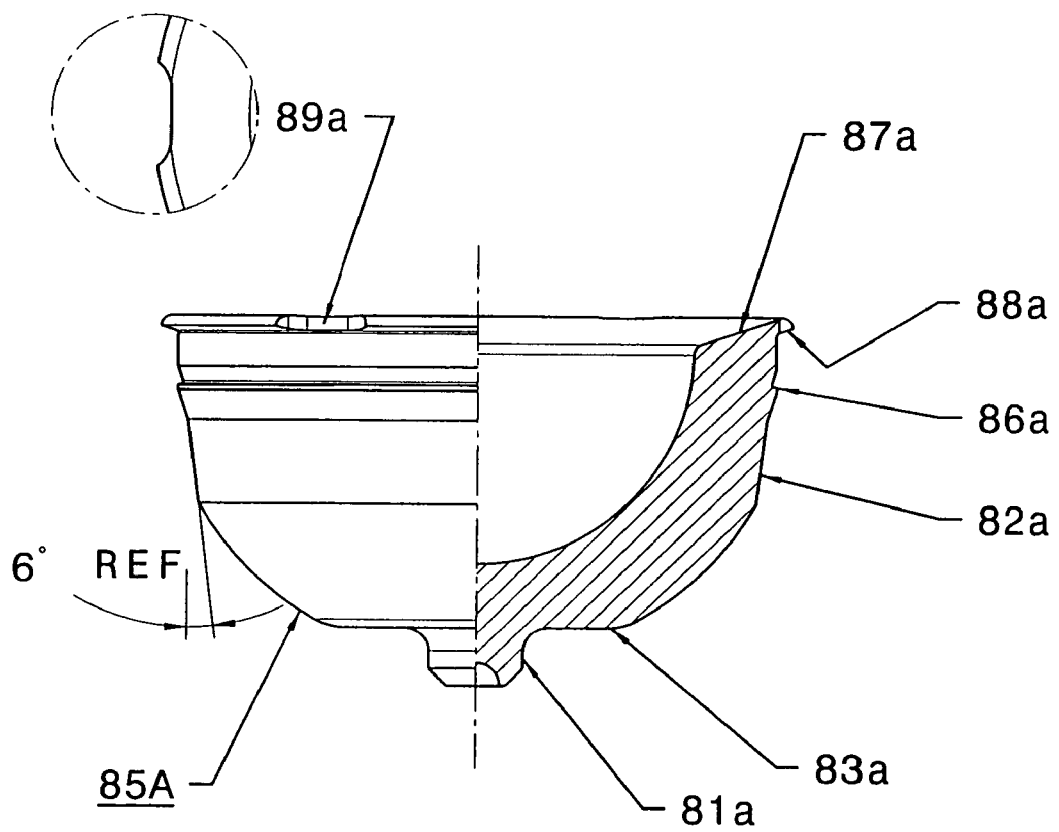
FIG. 8 is a partially sectioned view of the conical core illustrated in FIGS. 6 and 7.

FIGS. 6 and 7 show a non-retentive acetabular implant 80, that should be suitable for the majority of patients. The implant 80 shown in FIGS. 6 and 7 essentially differs from the implant illustrated in FIGS. 1 and 2 in that the core 85a is autoblocking and that there is no need for a threaded ring to secure the core 85A in position in the acetabular cup 46. More particularly, the implant 80 comprises an acetabular cup 46 similar to the one illustrated in FIGS. 1, 2 and 3. The core 85A (FIG. 8) in its part comprises at least one autoblocking tong 86a to engage with one of the ribs 20 of the acetabular cup 46. Therefore, the core 85A may be locked in two levels of insertion in the acetabular cup 46 depending on if the autoblocking tong 86a is engaged in the first rib 20 or in the second. The core 85A may also comprise two autoblocking tongs to engage with each of the ribs 20 of the acetabular cup 46 therefore procuring an additional degree of retention. The core 85A can be easily oriented by gradually driving the conical core towards the bottom 28 of the expandable acetabular cup 46 until an acceptably rigid position for verifying the orientation of the acetabular cup 46 with a guide/impacteur graduated in degrees. At this stage the core 85A may be retracted from its constrained position so as to be repositioned if necessary. The rib 89a of the core are created so that three sections of the guide/impacteur come into contact with the surface 87a of the core during the implantation and that the rim 88a can serve to retract the core if necessary.

According to installation procedures, the bone cavity is previously enlarged. The orientation of the acetabulum should be situated between an inclination of 35° and 45° and an antiversion between 10° and 20° as shown in FIG. 10. Once the position has been validated, the core 85a is maximally driven in depth and is guided by the pivot 81a in the central cavity 40 of the bottom 28 of the acetabular cup. It is the angular surface 82A of the core 85A that begins the radial expansion of the acetabular cup 46 by the pressure that is exerted on the surface 22; at this stage the repositioning may be effected by retracting the conical core 85A from its constrained position. When the surface 83a of the core 85A comes into contact with the bottom 28 of the acetabular cup 46, the blade 86a engages with the rib 20 of the expanded acetabular cup 46, therefore permitting for a solid engagement of the wall 34 with the bone tissue.

Figure 9:
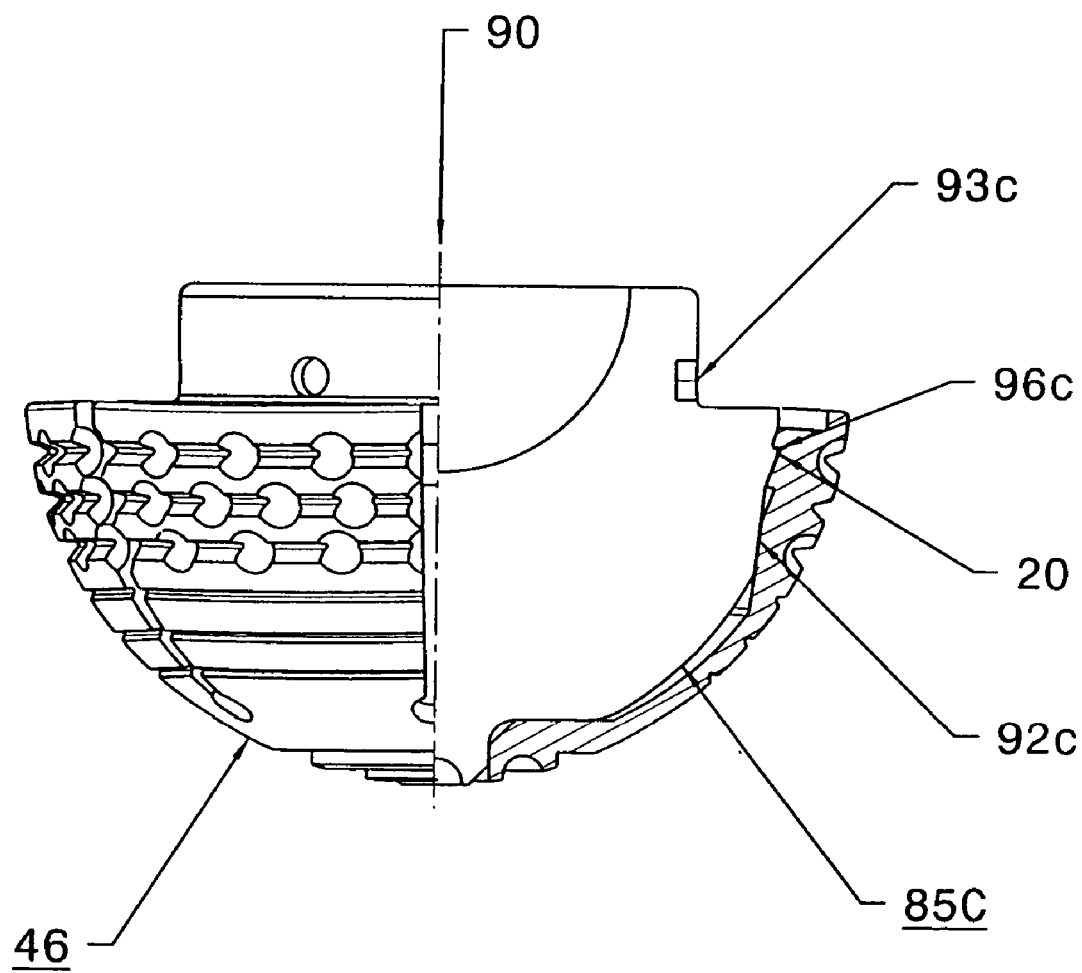
FIG. 9 is a partially sectioned view of an alternative assembly of a core with a neck.

FIG. 9 shows an alternative assembly of an acetabular cup having a neck, for this model, identified by the letter "C", it is the cavities 93c that permit the installation with the help of an orienting impactor according to the desired orientation shown in FIG. 10. The conical part 92c of the autoblocking core 85C permits the radial expansion of the acetabular cup 46. By driving the core 85c to a maximum depth, the tong 96c engages with the angular rib 20 of the expanded acetabular cup and secures the position of the core 85C in the expanded acetabular cup 46.

The invention claimed is:

1. An acetabular implant comprising an acetabular cup defining an internal cavity, the acetabular cup having a spikeless hemispherical outer surface, a plurality of circumferential grooves defined in the spikeless hemispherical outer surface, spaced-apart cavities defined along each of said circumferential grooves, the acetabular cup having a frustoconical internal surface defining a taper towards a bottom of the acetabular cup, at least two ribs provided on said frustoconical internal surface, and a conical core insertable in the internal cavity, the conical core having a frustoconical outer surface having a taper greater than the taper of said frustoconical internal surface of said acetabular cup, the at least two ribs on the frustoconical internal surface of the acetabular cup defining at least two insertion increments of the conical core in the acetabular implant, each increment corresponding to a different degree of expansion of the acetabular cup.

2. The implant as defined in claim 1, wherein said acetabular cup is substantially hemispherical and cut into sectors by slots oriented along meridian planes.

3. The implant as defined in claim 2, wherein said slots penetrate towards the bottom of said acetabular cup at about 55° from an opening plane of said acetabular cup.

4. The implant as defined in claim 3, wherein an angle of approximately 60° is defined between said slots.

5. The implant as defined in claim 1, wherein said core defines a housing in which a femoral head articulates.

6. The implant as defined in claim 5, wherein threads are defined on an exterior surface of said core for adjustment with a threaded ring for retaining said femoral head in said housing, said threaded ring having at least one stop for cooperating with said at least two ribs.

7. The implant as defined in claim 1, wherein the taper of said core is about 6°, while the taper of said internal surface is in the range of 4° to 5°.

8. The implant as defined in claim 1, wherein a central passage extends through the bottom of said acetabular cup.

9. The implant as defined in claim 8, wherein said core comprises a guide for slidably engaging in said central passage during the insertion of said core in said acetabular cup.

10. The implant as defined in claim 1, wherein said circumferential grooves are interrupted by radial slots dividing said acetabular cup in a given number of segments.

11. The implant as defined in claim 10, wherein said grooves are distributed starting from a superior rim of said acetabular cup, said grooves being parallel to an equatorial plane of said acetabular cup.

12. The implant as defined in claim 1, wherein said core comprises a principle body defining a housing for receiving a femoral head, and a threaded ring screwed onto said principle body to retain said femoral head in said housing, said threaded ring having at least a notch for engaging in a rib defined in said acetabular cup so as to lock said principle body in said acetabular cup.

13. An implant for insertion in an articular cavity previously enlarged, comprising a conical core, a prosthetic acetabular cup partially slotted at various locations for permitting radial expansion of said acetabular cup by said core and, thereby permitting anchoring of said acetabular cup in the articular cavity, the retraction of said core permitting said prosthetic acetabular cup to radially contract towards a relaxed position therefore facilitating the retraction of said acetabular cup from the articular cavity, the acetabular cup having a spikeless hemispherical exterior surface, circumferential ribs defined in said spikeless hemispherical exterior surface, circumferential arrays of spaced-apart cavities defined in the spikeless hemispherical exterior surface between adjacent circumferential ribs, the acetabular cup further having a frustoconical internal surface defining a taper towards a bottom of the acetabular cup, at least two angular ribs provided on said taper and defining two different levels of insertion of the conical core in the acetabular cup, each level of insertion providing a different degree of expansion of the acetabular cup, thereby providing for a stepped expansion and retraction of the acetabular cup by indexing the conical core between said at least two angular ribs.

14. An implant for placement into an articular cavity previously enlarged, comprising an expandable and retractable acetabular cup for being inserted in a bone cavity, a conical core for inserting under pressure in said acetabular cup and therefore causing radial expansion, said core being retractable from said acetabular cup for permitting radial contractions thereof towards an initial position therefore facilitating the repositioning of said acetabular cup, the acetabular cup having a frustoconical internal surface having a taper and at least two catching ribs, each catching rib defining a level of insertion of the conical core in the acetabular cup, said level of insertion corresponding to an associated degree of expansion of the acetabular cup, thereby allowing to incrementally expand and contract the acetabular cup by displacing the conical core from one catching rib to the other, the implant further comprising a ring adapted to be threadably engaged on the conical core to retain a femoral head in a cavity defined in the conical core, the ring having at least one stop defined on an outer surface thereof for cooperating with the at least two catching ribs in order to secure the conical core at two different levels of insertion in the acetabular cup.

15. The implant as defined in claim 14, wherein said acetabular cup is cut into sectors by partial radial slots.

* * * * *